US008622893B2

(12) United States Patent
Mathieu

(10) Patent No.: US 8,622,893 B2

(45) Date of Patent: Jan. 7, 2014

(54) MEDICAL APPLIANCE WITH A CONNECTION AND DISCONNECTION SYSTEM FOR A SEPARABLE MEDICAL INSTRUMENT

(75) Inventor: Nicolas Mathieu, Ecully (FR)

(73) Assignee: Axess Vision Technology, Tours (FR)

( * ) Notice: Subject to any disclaimer, the term of this patent is extended or adjusted under 35 U.S.C. 154(b) by 655 days.

(21) Appl. No.: 12/746,833

(22) PCT Filed: Dec. 11, 2008

(86) PCT No.: PCT/FR2008/052277

§ 371 (c)(1), (2), (4) Date: Aug. 25, 2010

(87) PCT Pub. No.: WO2009/080996

PCT Pub. Date: Jul. 2, 2009

(65) Prior Publication Data

US 2010/0324368 A1 Dec. 23, 2010

(30) Foreign Application Priority Data

Dec. 11, 2007 (FR) .................................... 07 59713

(51) Int. Cl.
*A61B 1/00* (2006.01)

(52) U.S. Cl.
USPC ............ 600/132; 600/136; 600/146; 600/147

(58) Field of Classification Search
USPC ................ 600/113–114, 121–122, 132, 136, 600/146–148
See application file for complete search history.

(56) References Cited

U.S. PATENT DOCUMENTS

| | | | |
|---|---|---|---|
| 8,070,685 B2 * | 12/2011 | Harhen et al. | 600/146 |
| 2005/0177027 A1 | 8/2005 | Hirata | |
| 2005/0191046 A1 | 9/2005 | Dehmel et al. | |
| 2005/0192565 A1 | 9/2005 | Eum et al. | |
| 2006/0052664 A1 * | 3/2006 | Julian et al. | 600/146 |
| 2006/0178560 A1 * | 8/2006 | Saadat et al. | 600/114 |
| 2006/0287576 A1 * | 12/2006 | Tsuji et al. | 600/132 |
| 2008/0125628 A1 * | 5/2008 | Ueno et al. | 600/130 |

FOREIGN PATENT DOCUMENTS

| | | | |
|---|---|---|---|
| FR | 2794535 | 12/2000 | |
| WO | PCT/JP2006/311117 | * 12/2006 | A61B 1/00 |

* cited by examiner

*Primary Examiner* — Matthew J Kasztejna
*Assistant Examiner* — Kevin G Barry, III
(74) *Attorney, Agent, or Firm* — Ladas & Parry LLP

(57) ABSTRACT

A medical appliance including a medical instrument that is separable from an actuator support, the appliance including a connection and disconnection system including a connector carried by the instrument and including a guide for guiding at least one actuator rod retained elastically in the guide by a head, and a coupling endpiece carried by the support and including at least one engagement mechanism that is guided in rotation and that defines a reception setback for receiving the head of the actuator rod. The engagement mechanism is fitted with a rotary coupling member complementary to the rotary coupling member presented by the connector, and the endpiece also presents at least one hook connected to an actuator system.

19 Claims, 7 Drawing Sheets

MEDICAL APPLIANCE WITH A CONNECTION AND DISCONNECTION SYSTEM FOR A SEPARABLE MEDICAL INSTRUMENT

BACKGROUND OF THE INVENTION

The present invention relates to the technical field of medical appliances in the general sense, and more particularly it relates to the technical field of appliances comprising a medical instrument that is separable from an actuator support.

More precisely, the invention provides a medical appliance in which the actuator support is designed to be reusable, while the medical instrument that comes into contact with human tissues or organs is for single use only, or for multiple uses but with the same patient.

In the state of the art, numerous medical appliances are known that implement a single-use medical instrument. For example, in the field of endoscopy, U.S. Pat. No. 4,919,112 describes a flexible tubular instrument that is mounted by means of a connection and disconnection system to an actuator support that forms a handle. The flexible tubular instrument includes a threaded coupling having a rocker lever having fastened to each end thereof a respective cable that is fastened to the free end of the flexible tubular instrument to enable it to be folded or deflected.

That flexible tubular instrument is fastened to the handle by means of a threaded ring that co-operates with the threaded coupling. The handle includes a pair of actuator rods that are controlled to move in synchronized alternating linear movements so as to press successively against one or the other of the ends of the cable-actuating lever. Thus, one of the cables is moved in one direction while the other cable is caused to move in the opposite direction. It should be observed that in that solution there is no mechanical connection between the cables and the actuating rods, insofar as the rods provide thrust movement only. That solution presents the drawback of limiting the mechanical movements that are transmitted to the medical instrument.

Similarly, US patent application No. 2005/177027 describes an endoscope including electrical connection means between an insertion tube and an observation head. The observation head includes an annular electrode connected to light-emitting diodes that are implanted at the free end of the head. That annular electrode is made up of a stack of three connection sheets and is located at the rear of the head, so as to be in electrical contact with electrodes that extend to the end of the insertion tube.

The observation head includes an assembly ring provided internally with two threads. The insertion tube is provided at its free end with a thread that is engaged axially inside the ring that is turned so as to ensure screw fastening of the insertion tube with the observation head. At the end of the assembly stroke, the electrodes of the insertion tube are in electrical contact with the electrodes so as to power the light-emitting diodes electrically.

That document describes an endoscope including a system for providing electrical connection by moving an observation head and an insertion tube towards each other with the help of a screw-and-nut system. That document does not describe a connection and disconnection system suitable for providing a genuine mechanical connection that can be separated easily and quickly between a medical instrument and an actuator support.

SUMMARY OF THE INVENTION

The subject matter of the invention seeks to remedy the drawbacks of the state of the art by proposing a novel medical appliance including a connection and disconnection system for a separable medical instrument, and making it possible to provide a genuine separable mechanical connection between a medical instrument and an actuator support.

To achieve such an object, the medical appliance of the invention comprises a medical instrument separable from an actuator support, the appliance including a connection and disconnection system between the instrument and the support.

According to the invention, the connection and disconnection system comprises:

- a connector carried by the instrument and including a guide for at least one actuator rod held resiliently in the guide by a head projecting from the free end of the guide, the connector being provided with a rotary coupling member; and
- a connection endpiece carried by the support and including at least one engagement mechanism guided in rotation and defining a reception setback for receiving the head of the actuator rod, the mechanism being fitted with a rotary coupling member complementary to the rotary coupling member presented by the connector, the endpiece also presenting at least one hook connected to an actuator system, the endpiece and the connector occupying a connection position after they have approached each other axially leading firstly to rotary coupling between the connector and the engagement mechanism and secondly to disengagement of the head of the rod from the guide so that said head is engaged inside the reception setback presented by the engagement mechanism, axial approach being followed by a movement in rotation between the connector and the connection endpiece to turn the engagement mechanism so as to move the head of the rod until it co-operates with the hook in order to provide a mechanical connection between the head of the rod and the actuator hook.

The connection and disconnection system is adapted to separate the medical instrument easily from the support by performing a turning movement in the direction opposite to that used for obtaining the connection. Thus, in the connected position, the support and the medical instrument are moved relative to each other in opposite rotation to turn the engagement mechanism, which is adapted to disengage the head of the rod from the hook in such a manner as to enable an axial separation movement between the support and the medical instrument to disconnect the medical instrument from the actuator support.

In an embodiment, at least one hook possesses a reception housing for receiving a head of the rod in order to provide a connection in translation between the rod and the actuator hook.

In another embodiment, at least one hook possesses a housing of prismatic shape suitable for receiving a complementary prismatic head of a rod in order to provide a connection in translation and/or rotation between the rod and the actuator hook.

Preferably, the hook possesses a positioning groove for the rod, which groove is formed between the reception housing for the head and the free end of the hook.

In the embodiment shown, in the position waiting for connection, the engagement mechanism is mounted to extend inside the hook with the setback situated outside the hooks, so as to receive the head of a rod after the approach movement, the engagement mechanism extending, after movement in rotation, outside the hook that is positioned inside the setback in order to be able to slide freely.

In an advantageous embodiment, the connection endpiece is provided with at least one optical, electrical, fluid-flow, or mechanical-passage coupling member, and the guide of the connector is provided with at least one complementary coupling member that is respectively optical, electrical, fluid-flow, or for providing mechanical passage, that is adapted to be aligned with the coupling member of the endpiece as a result of establishing mechanical connection between the rod and the actuator hook.

For example, the coupling member passes through the engagement mechanism via a setback adapted to ensure that said member is not moved by the engagement mechanism when it turns, said member being located substantially at the free end of the hook.

According to another characteristic of the invention, the support includes a body that is cutout to present a series of bars, at least one of which is movable linearly relative to the other bars, thereby constituting a slideway-forming part of the system for actuating a hook.

Advantageously, each slideway-forming bar is provided with a hook at one of its ends, while its other end is connected to a translation actuator member.

In an embodiment, at least one bar incorporates an actuator system for actuation in rotation and/or in translation.

In another embodiment, at least one bar serves to position an optical, electrical, fluid-flow, or mechanical-passage coupling member.

Advantageously, the connector and the connection endpiece include angular indexing means enabling them to be aligned in a predetermined position for their axial approach.

According to a preferred embodiment characteristic, the connector and the endpiece include guide means for providing guidance in sliding for the axial approach and then in rotation to an abutment position corresponding to the connected position of the connection and disconnection system.

Preferably, the connector and the endpiece include locking means for locking the connector and the endpiece in their connected position.

In an embodiment, the locking means include a single-use locking indicator carried by the connector, which means serve, after the instrument has been disconnected following use, to prevent reconnection of the instrument to the support.

In another embodiment, the locking means include a reusable locking indicator that is carried by the connector or by the coupling endpiece, and that acts, after disconnection of the instrument, to enable the instrument to be reconnected to the support.

For example, the actuator rod is a flexible element such as a cable, or a rigid element such as a rigid shaft.

As an example application, the separable medical instrument constitutes all or part of a surgical tool, a catheter, an endoscope, or a probe.

In a particular application, the medical instrument is an endoscope or a catheter including a tubular sheath fastened to the connector and having at least one actuator rod fastened to the end thereof for steering the head of the sheath.

Advantageously, the tubular sheath includes at least one optical, electrical, fluid-flow, or mechanical-passage coupling member for single use and complementary to at least one respective optical, electrical, fluid-flow, or mechanical-passage coupling member mounted in the coupling endpiece.

BRIEF DESCRIPTION OF THE DRAWINGS

Various other characteristics appear from the following description made with reference to the accompanying drawings that show embodiments of the invention by way of non-limiting example.

DESCRIPTION OF THE PREFERRED EMBODIMENTS

As shown in the figures, the subject matter of the invention relates to a medical appliance 1 comprising at least one separable medical instrument 2 and a support or actuator block 3 that is preferably in the form of a handle or of a robot arm. By way of example, the medical instrument 2 constitutes all or part of a surgical tool, a catheter, an endoscope, or a probe.

Figure 1:
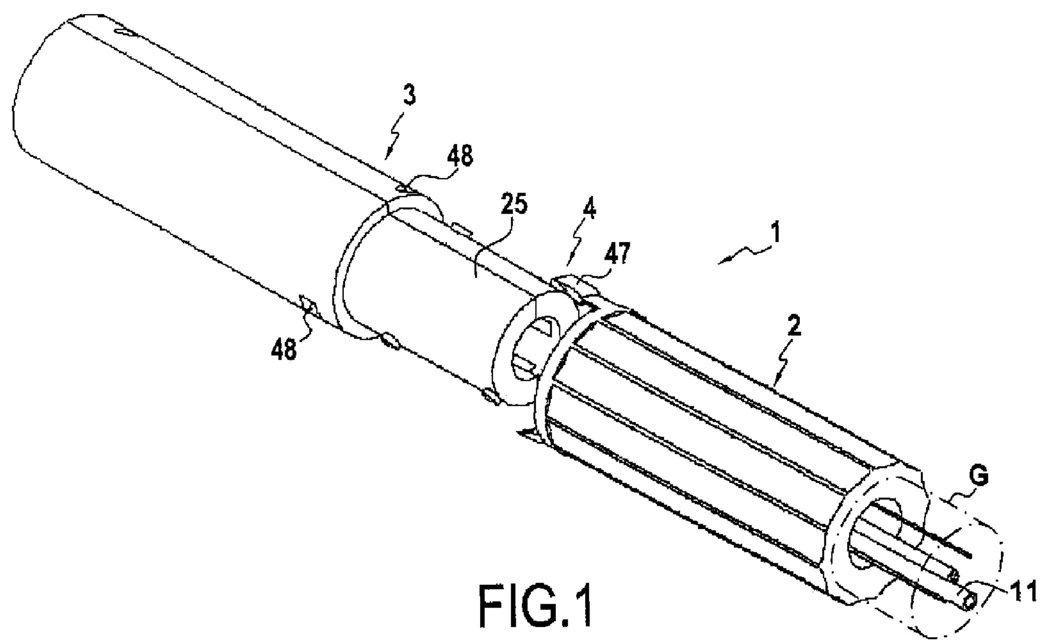
FIGS. 1 and 2 are respective views of a medical appliance in accordance with the invention shown respectively in a disconnection position and in a connection position.
Figure 2:
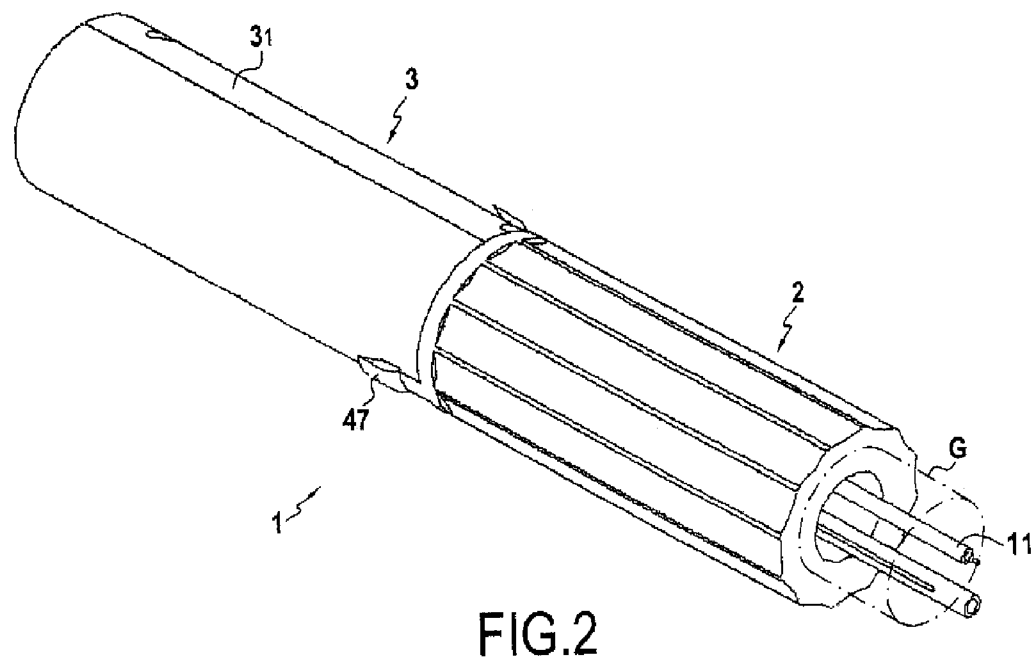
Figure 3:
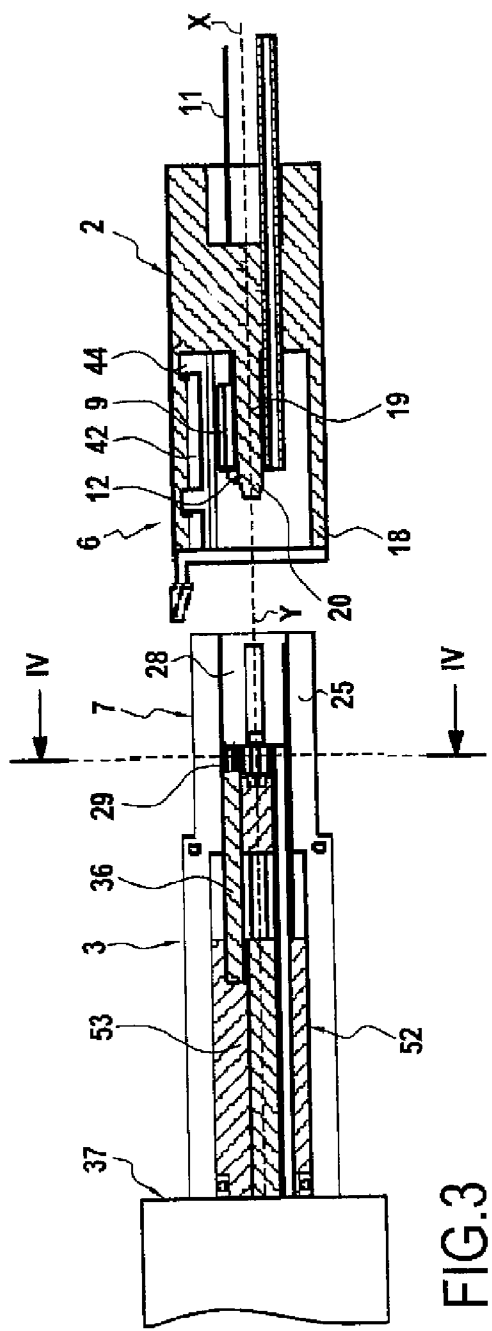
FIG. 3 is an elevation view in section of a medical appliance in the disconnection position.

The medical appliance 1 has a connection and disconnection system 4 between at least one medical instrument 2 and the support 3, the system being adapted to act quickly to provide a temporary connection that is at least mechanical, while offering the advantage of enabling the medical instrument 2 to be separated easily. Thus, the medical instrument 2 and the support 3 are moved relative to each other in order to go from a disconnection position (FIG. 1) to a connection position (FIG. 2). After the medical instrument 2 has been used, the support 3 and the medical instrument 2 are moved so as to go from the connection position to the disconnection position in order to enable the medical instrument 2 to be changed. Preferably, the medical instrument 2 is for single use, or for multiple uses on the same patient.

As can be seen very clearly in FIGS. 3 to 6, the connection and disconnection system 4 comprises a connector 6 of longitudinal axis X that is carried by the medical instrument 2 and that is designed to co-operate with a connection endpiece 7 of longitudinal axis Y that is carried by the support 3. The connector 6 includes a guide 9 for at least one, and in the example shown for three actuator rods 11 that are in flexible form so as to constitute a cable, or in rigid form so as to form a shaft or a link. In the embodiment, the medical instrument 2 has a rigid rod 11 and a set of two flexible actuator rods 11 with ends (not shown) for connection to means that are adapted to the type of medical instrument 2. For example, one rod 11 is connected to a tool, while the other two rods 11 are connected to a flexible sheath G to enable it to be folded, deflected, extended, or retracted, or to generate pressure or suction acting directly or indirectly.

Each actuator rod 11 is held resiliently in the guide 9 by a head 12 that projects from the free end of the guide 9. Each end of the rod 11 is provided with a head 12, e.g. of hemispherical or prismatic shape, that projects from the transverse end face $\mathbf{9}_1$ of the guide 9. The guide 9 possesses a cylindrical shape and is arranged to present at least one, and in the example shown three grooves 14 each surpassing one rod 11. Each groove 14 passes right through the guide 9 along the longitudinal axis X and opens out into the periphery of the guide 9. Advantageously, each groove 14 is arranged to extend along a circular segment centered on the longitudinal axis X and co-operating with the periphery of the guide to define a radial retaining wall 15 for the rod 11 that is engaged in said groove 14. In the embodiment shown, two passage grooves 14 extend in symmetrical opposite positions about the longitudinal axis X so as to enable action to be taken on two points of a radial section of the sheath G, for example. Naturally, different angular positions may be envisaged for the grooves 14, and a different number of grooves may be envisaged, depending on the number of actuator rods 11 implemented.

A return spring 17 serves to urge the rods 11 so that the heads 12 are held pressed against the transverse end face $\mathbf{9}_1$. In the example shown, the spring 17 is interposed between the transverse face $\mathbf{9}_2$ of the guide that is remote from its transverse end face $\mathbf{9}_1$ and the connector 6 to which the rods 11 are mechanically connected. It should be observed that the guide 9 is held in translation and in rotation by the pressure of the spring 17 acting on the projecting heads 12, thereby enabling the connector to be held in a position waiting for connection.

Advantageously, the connector 6 is in the form of a body that is arranged to present on its front face a tubular engagement sleeve 18 having the guide 9 mounted therein on a stud 19 that extends from the body of the connector, in the center of the sleeve and coaxially with the sleeve 18.

According to another characteristic, the connector 6 has a rotary coupling member 20. In the example shown, this coupling member 20 is constituted by a male prismatic shape fitted to the free end of the stud 19. Thus, this male prismatic shape projects relative to the guide 9 while being set back relative to the free end of the coupling sleeve 18.

Figure 4:
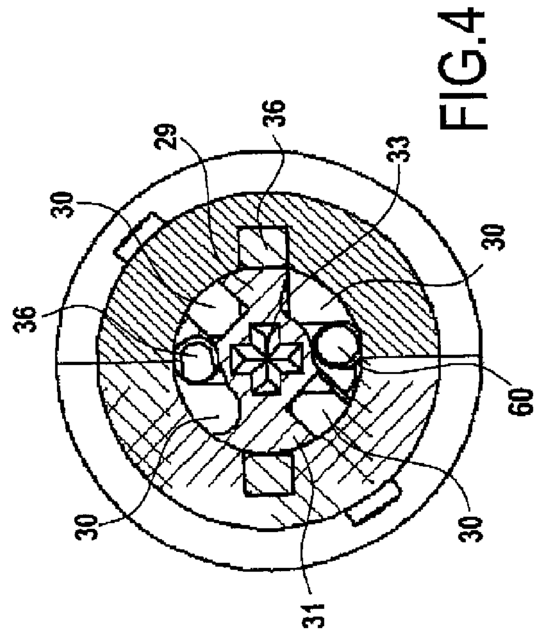
FIG. 4 is a view in cross-section taken substantially on line IV-IV of FIG. 3.
Figure 6:
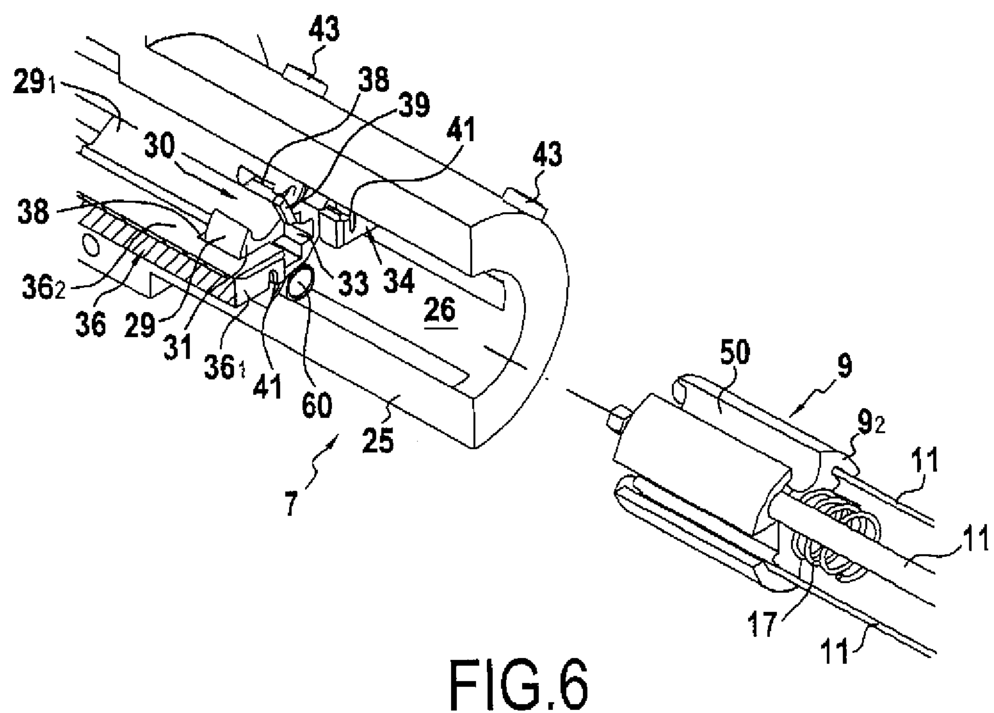
Figure 6A:
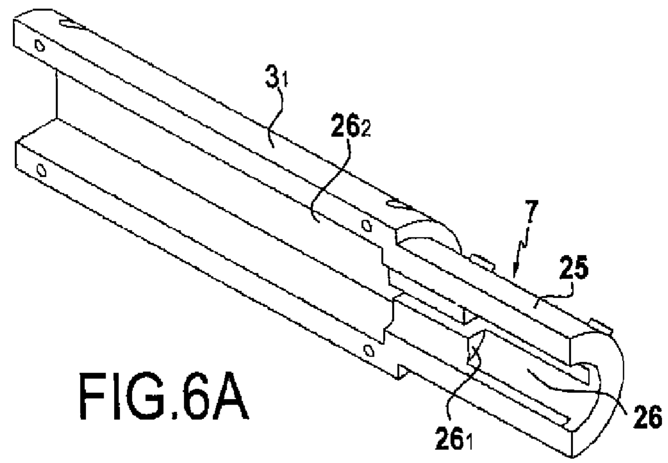
FIG. 6A is a view showing only the body of the support.

The connector 6 is designed to co-operate with the coupling endpiece 7 of the support 3. For this purpose, the coupling endpiece 7 presents a tubular coupling nose 25 that is designed, as explained in greater detail below, to engage between the tubular sleeve 18 and the guide 9 of the connector 6. The coupling nose 25 defines internally a bore 26 in which at least one engagement mechanism is mounted, such as an engagement cam 29 guided in rotation about the axis Y. The cam 29 is in the form of a disk extended by an assembly shank $\mathbf{29}_1$. The cam 29 is mounted in abutment against the end $\mathbf{26}_1$ of the bore 26 (FIG. 6A) that opens into another bore $\mathbf{26}_2$ that is coaxial therewith and that is defined by a tubular body $\mathbf{3}_1$ of the support 3. The cam 29 defines at least one, and in the example shown three setbacks 30 each for receiving one head 12 of a rod 11. The setbacks 30 open out to the transverse end face 31 of the cam (FIGS. 4 and 6). Naturally, the setbacks 30 are distributed in an angular disposition that is identical to that of the head 12 of the rods that are to penetrate together into the insides of the setbacks 30, merely by moving in translation, as described in the description below.

The cam 29 is fitted with a rotary coupling member 33 complementary to the rotary coupling member 20 presented by the connector 6. In the example shown, this rotary coupling member 33 is of a female prismatic shape arranged in the transverse face 31 of the cam and complementary to the male prismatic shape 20.

The coupling endpiece 7 also has at least one, and in the example shown three hooks 36 connected to an actuator system 37. The three hooks 36 are arranged to extend inside the bore 26. Each hook 36 is in the form of an elongate body extending parallel to the axis Y. In the example shown, two hooks 36 are disposed in symmetrically opposite manner about the axis Y. Each hook 36 includes a housing 38 for receiving the head 12 of a rod 11. Each housing 38 opens radially to the inside of the bore 26 so as to be bordered on one side by a distal radial branch $\mathbf{36}_1$ extending parallel to and at a distance from a proximal radial branch $\mathbf{36}_2$.

Each housing 38 is of a shape that is adapted to the head 12 that it receives. Thus, one of the hooks 36 possesses a housing 38 of prismatic shape complementary to the prismatic shape of the head 12. The other two hooks 36 in the example shown present housings 38 of rectangular shape adapted to receive the hemispherical head that is to come to bear via its base against the proximal radial branch $\mathbf{36}_2$.

Figure 5:
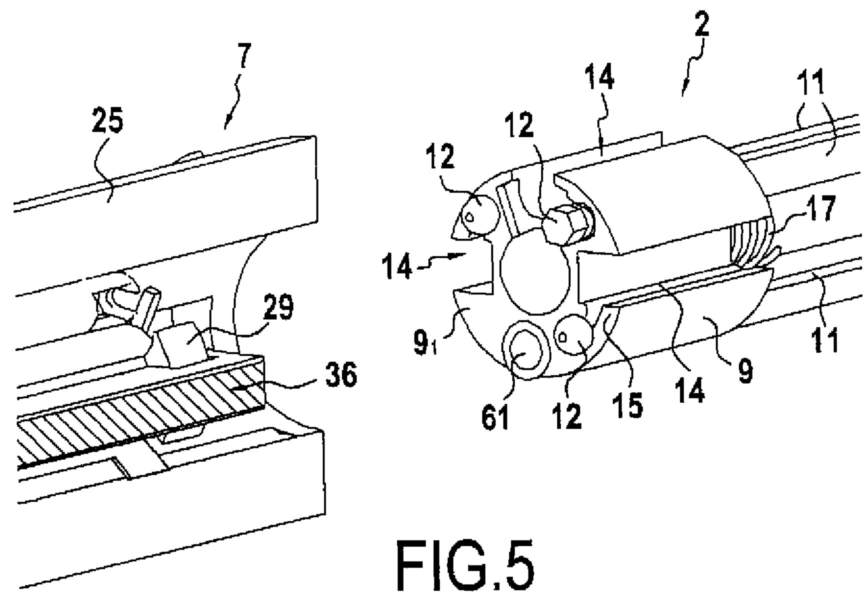
FIGS. 5 and 6 are fragmentary perspective views of the medical appliance in its position prior to connection.

In a neutral position waiting for connection, as shown in FIGS. 4 to 6, the hooks 36 are arranged in such a manner that the housings 38 are in alignment in a common plane extending transversely to the axis Y. Advantageously, the cam 29 is mounted so that its circular rotary path that is established in a plane perpendicular to the axis Y opens out into the housings 38. It should be understood that in this neutral position, the cam 29 is engaged in at least some of the housings 38, while the setbacks 30 of the cam extend outside the hooks 36 to receive the heads 12 that are to be moved by the cam 29. The cam 29 is arranged to receive the heads 12 and to move them angularly in both directions of rotation of the cam 29, as is explained below.

It should be observed that provision may be made for holder means for holding the cam 29 in this position waiting for connection. For example, these holder means may be implemented by a needle ball screw. Advantageously, the cam 29 prevents the hooks 36 from sliding and enables the hooks to be positioned in their position waiting for connection.

Operation of the above-described connection and disconnection system 4 stems directly from the above description.

Figure 7:
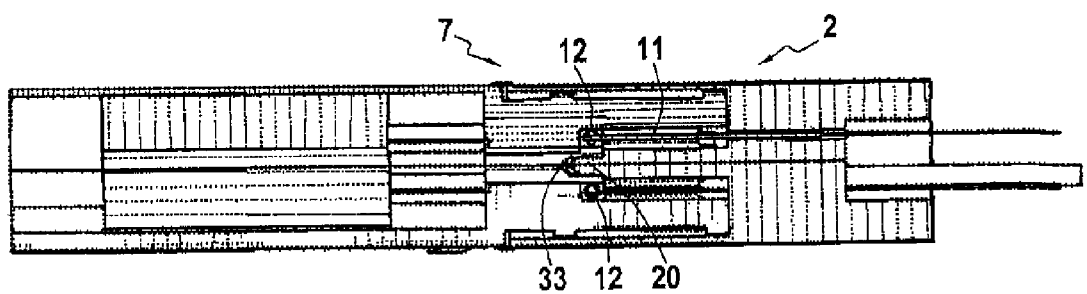
FIG. 7 is an elevation view showing a medical appliance in an intermediate connection position.
Figure 8:
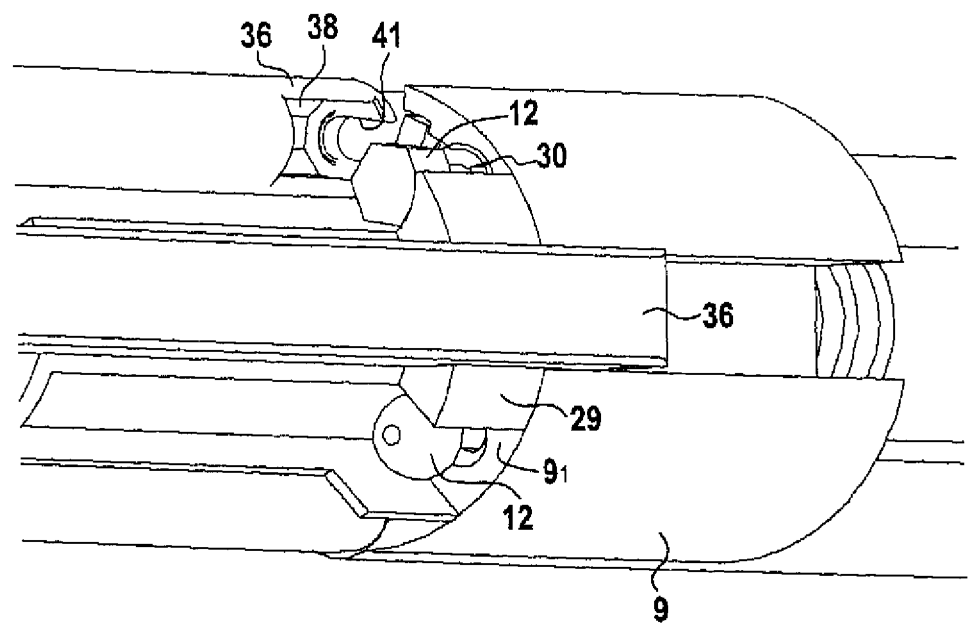
FIG. 8 is a perspective view of the medical appliance in the intermediate position shown in FIG. 7.
Figure 9:
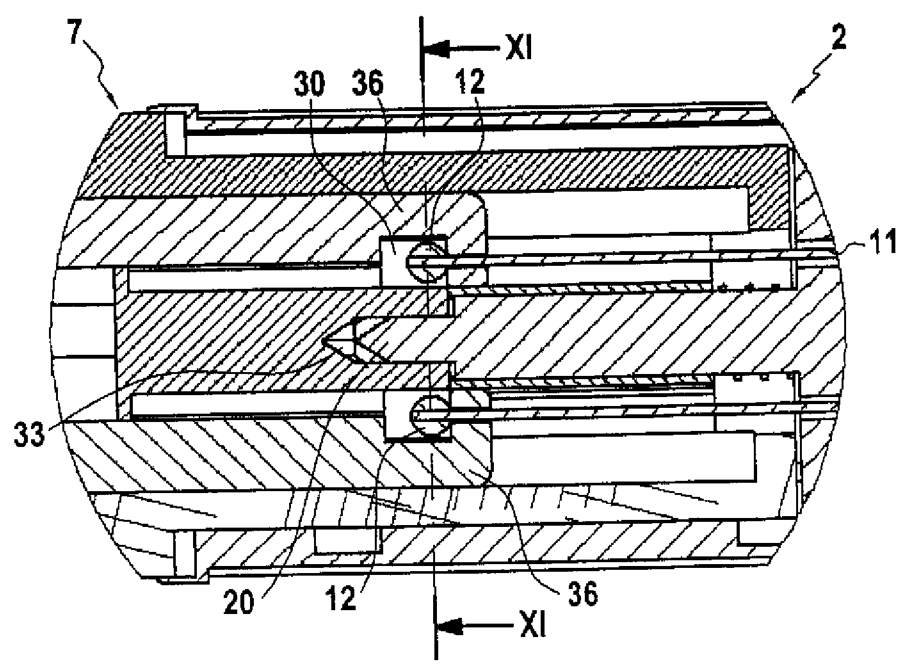
FIGS. 9 and 10 are angularly offset elevation views in section showing the medical appliance in the connection position.
Figure 10:
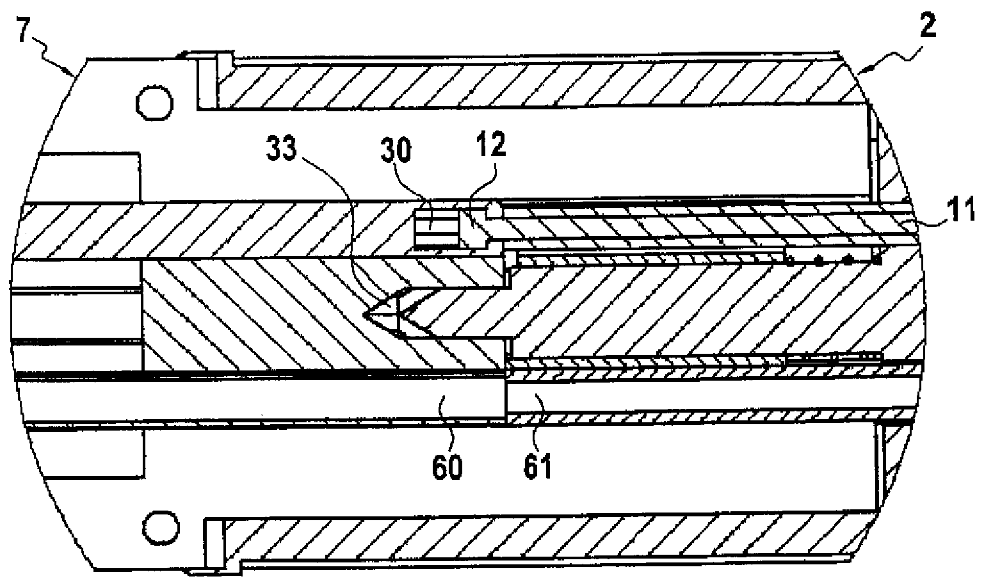
Figure 11:
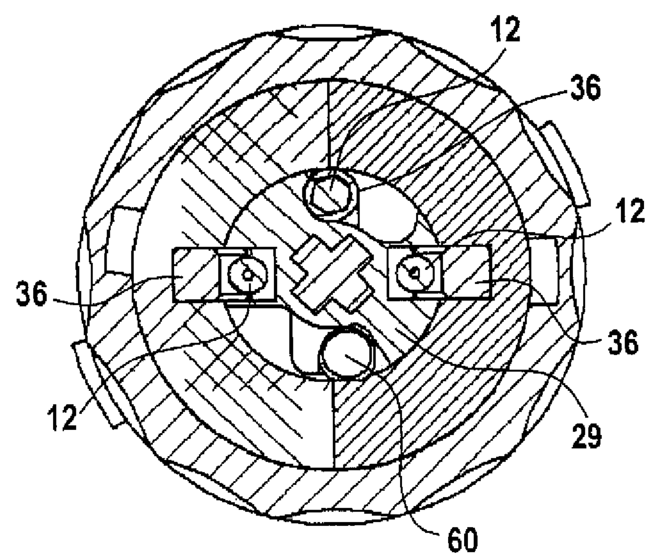
FIG. 11 is a cross-section view taken substantially on lines XI-XI of FIG. 9.
Figure 12:
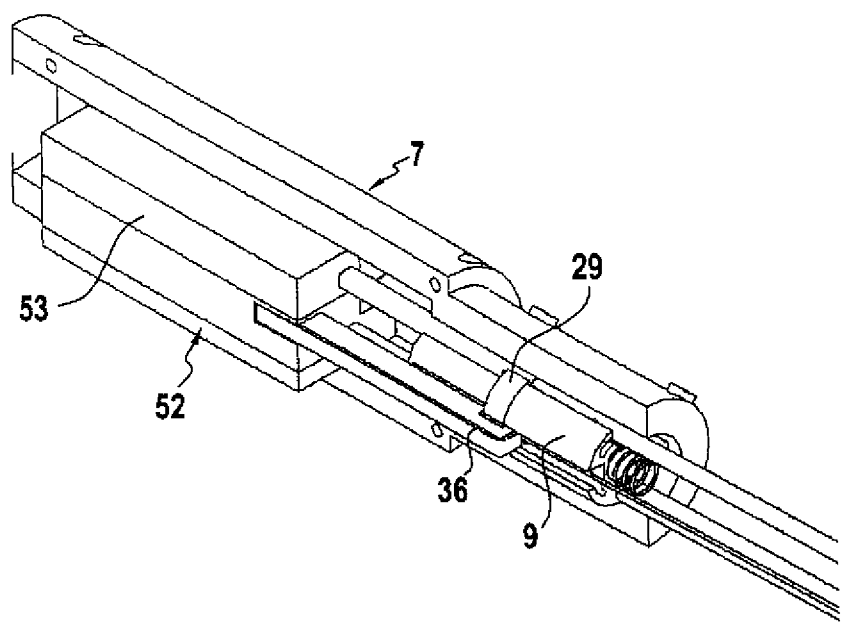
FIGS. 12 and 13 are perspective views of the medical appliance in the connection position, respectively before and after moving an actuator rod in translation.

Assembling a medical instrument 2 to an actuation support 3 starting from a position waiting for connection consists in providing axial and angular alignment between the connector 6 and the connection endpiece 7 before approaching them axially towards each other. The axial approach movement leads to the coupling nose 25 engaging between the sleeve 18 and the guide 9 of the medical instrument 2. The support 3 and the medical instrument 2 are positioned angularly relative to each other in such a manner that each head 12 is situated in alignment with a setback 30 of the cam 29. The axial movement is continued until the guide 9 comes to bear against the cam 29. Continuing the axial movement of the connector 6 leads to the spring 17 being compressed and to the heads 12 separating from the transverse face $\mathbf{9}_1$ of the guide 9, as can be seen more clearly in FIGS. 7 and 8. In this position, the male prismatic shape 20 of the connector 6 is engaged in the female prismatic shape 33 of the cam. In this position, each head 12 projects from the transverse face $\mathbf{9}_1$ and is positioned in a setback 30 of the cam, in register with a housing 38 of a hook. In other words, the heads 12 are placed in the plane of rotation of the cam 29.

Relative rotary movement between the connector 6 and the support 3 causes the cam 29 to turn, thereby turning each head 12 until it co-operates with the neighboring hook 36. At the end of this turning movement, each head 12 is positioned inside a housing 38 of a hook (FIGS. 9 to 12). In this position, the cam 29 extends outside the hook 36 so that the hook 36 is positioned inside the setback 30 of the cam, thereby enabling the hook 36 to slide freely. The connection and disconnection system 4 thus enables a mechanical connection to be established between the medical instrument 2 and the actuator support 3 by engaging each head 12 of a rod in a hook 36.

From the above description, it can be seen that the connection and disconnection system 4 makes it possible to obtain mechanical assembly of the medical instrument 2 with the support 3 by ensuring, once they are angularly and axially aligned, that they can approach each other axially and then turn relative to each other. Naturally, the transition from the connected position to the disconnected position consists in proceeding in the opposite manner, i.e. in effecting relative turning between the support 3 and the medical instrument 2 in the opposite direction so that the cam 29 causes the heads 12 to turn and makes them escape from the housings 38 of the hooks 36. At the end of this turning movement, the heads 12 are situated outside the hooks 36 and extend inside the setbacks 30. Moving the medical instrument 2 and the support 3 apart from each other in an axial direction then enables them to be separated.

It should be observed that the cam 29 serves to engage the heads 12 in the hooks 36 in one direction of rotation and to disengage them when rotary movement is performed in the opposite direction. Thus, the cam 29 includes abutment surfaces defining opposite sides of the setbacks 30 and adapted to turn the heads in both directions of rotation of the cam. In an embodiment, the cam 29 is provided with an ejector 39 to ensure that the primsatically-shaped head 12 moves out from its housing 38.

Depending on the shape of the head 12, a connection may be obtained in translation and/or in rotation between the rod 11 and the associated hook 36. Preferably, each hook 36 possesses a positioning groove 41 for the rod 11 that is arranged between the reception housing 38 and the free end of the hook. This groove 41 enables the rod 11 to be maintained in a straight position without being curved, with the head 12 centered in its housing 38.

In an embodiment, the connector 6 and the connection endpiece 7 include angular indexing means enabling them to be aligned in a predetermined position for moving towards each other axially. These indexing means (not shown) enable the user to orient the medical instrument 2 at an appropriate angle relative to the support 3 so as to ensure that the heads 12 of the rods are in alignment with the setbacks 30 of the cam 29. For example, the indexing means may be implemented as marks formed on the connector 6 and the connection endpiece 7, such that when they are in alignment, the medical instrument 2 and the support 3 are in position for approaching each other axially.

In a preferred embodiment, the connector 6 and the endpiece 7 include means for providing guidance from sliding while they are approaching each other axially and then in rotation to an abutment position that corresponds to the position in which the connection is established with the connection and disconnection system 4. In the embodiment shown, the guide means comprise a groove 42 arranged in the inside face of the sleeve 18 and extending parallel to the longitudinal axis X of the connector. In complementary manner, the tubular coupling nose 25 is provided on its outside face with two lugs 43 in alignment on a straight line parallel to the axis Y of the support 3. During connection of the medical instrument 2, the support 3 is angularly positioned relative to the medical instrument so as to engage the two lugs in the guide 18. Naturally, this positioning corresponds to the position for axial approach enabling the heads 12 to be engaged in the setbacks 30. It should be observed that the angular indexing means are implemented to show the angular positioning between the support 3 and the medical instrument 2.

The turning guide means are implemented by two grooves 44 formed in the inside face of the sleeve 18 over angular sectors lying in mutually parallel planes that are perpendicular to the longitudinal axis X. These grooves 44 open out into the groove 42 at the positions where the lugs 43 are located at the end of the axial approach movement between the medical instrument 2 and the support 3. The length of the grooves 44 is determined so as to bring the lugs 43 into abutment against the ends of the grooves in a position that corresponds to connection with the connection and disconnection system 4.

In an embodiment, the connector 6 and the endpiece 7 include means for locking the connector and the endpiece in their connected position. In other words, the connector 6 and the endpiece 7 include means enabling the system 4 to pass from its connection position to its disconnection position. For example, these locking means may be implemented in the form of slots formed in the bottoms of the grooves 44 to constitute abutments preventing the lugs 43 from returning in an opposite direction, enabling the lugs to be brought into their connection position. Naturally, the locking means could be provided in some other way, for example, as shown in FIGS. 1 and 2, by implementing tabs 47 that project from the sleeve 18 and that are designed, in the connection position, to co-operate with cavities 48 formed in the outside of the body $\mathbf{3}_1$ of the support 3.

It should be noted that provision may be made for the medical instrument 2 to possess a utilization indicator so that it can be determined whether the medical instrument has or has not been connected to a support 3.

In an embodiment, the locking means include a locking indicator for informing the user that the medical instrument 2 is in the connected position. In this embodiment, the locking indicator is for single use. For example, the locking indicator may be carried by the medical instrument and may be damaged after the medical instrument 2 has been disconnected from the support 3. Under such conditions, the medical instrument 2 can no longer be mounted in a locked position relative to the support 3 insofar as the locking indicator has been damaged. By way of example, the single-use locking indicator may be implemented by the tabs 47 that are adapted to break while the medical instrument 2 is being disconnected from the support 3. In another embodiment, the locking indicator carried by the connector or by the connection endpiece may be suitable for reuse so as to make it possible, after the medical instrument 2 has been disconnected, for the medical instrument 2 to be connected once more to the support 3. This solution provides the advantage of enabling a medical instrument to be used several times over for a given patient with a support 3 that is also used by some other medical instrument.

As can be seen from the above description, the connection and disconnection system 4 serves to provide a mechanical connection between the support 3 and the medical instrument 2 that enables movement to be transmitted in translation in both directions and/or in rotation. It should be observed that for a connection in translation, the guide 9 is provided with grooves 50 that are parallel to the longitudinal axis X. These grooves 50 are adapted to enable a hook 36 to be received or even guided during its movements in translation.

Figure 13:
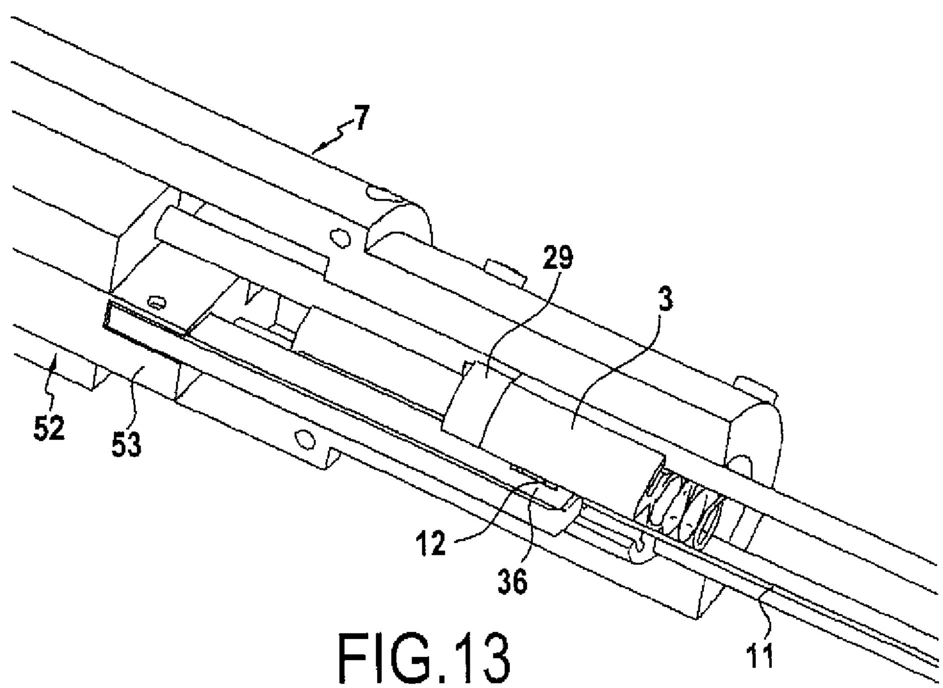

In an embodiment, the hook actuation system 37 comprises a cutout body 52 mounted inside the body $\mathbf{3}_1$ of the endpiece 7. This body 52 is cut out so as to present a series of bars 53, at least one of which can be moved linearly relative to the other bars so as to constitute a slideway for actuating a hook 36. In the example shown, each slideway-forming bar is provided at one of its ends with a hook 36 (FIG. 13), while its other end is connected to a member for actuating it in translation, which member is not shown but may be of any known type. Thus, each bar 53 may be connected, e.g. directly or via a movement-transforming system, to a motor or to a piston. For example, the movement-transformation system may be of the wormscrew-and-nut type or of the rack-and-pinion type, with one of the elements secured to the bar 53. In another embodiment, provision may be made for a bar 53 to incorporate an actuator system operating in rotation and/or in translation. Thus, provision may be made for the bars 53 to be movable relative to one another, being guided in translation relative to one another. In this embodiment, the bars 53 possess shapes that are defined by plane faces. Provision could also be made for some of the bars 53 to be stationary.

In the above description, the connection and disconnection system 4 provides a mechanical connection between the medical instrument 2 and the actuator support 3. In an embodiment, it should be observed that the connection and disconnection system 4 also serves to provide a coupling of a different kind, e.g. optical, electrical, fluid-flow, or to provide a coupling suitable for mechanically passing a mechanism of any kind.

In this embodiment, the connection endpiece 7 is provided with at least one optical, electrical, fluid-flow, or mechanical-passage coupling member 60. The guide 9 of the connector 6 is also provided with at least one complementary coupling member 61 that is respectively optical, electrical, fluid-flow, or for mechanical passage, and that is adapted to be in alignment with the coupling member 60 of the endpiece, once mechanical connection has been established between the rod 11 and the actuator hook 36. It should be observed that the coupling member 60 passes through the engagement cam 29 via a setback 30 adapted so that said member 60 is not moved by the cam 29 when it turns (FIG. 4). Preferably, this coupling member 60 lies substantially at the free end of the hook 36 so as to make it possible to obtain a coupling or connection with the complementary coupling member carried by the medical instrument 2. It should be observed that this coupling member 60 is mounted in a bar 53 that may be mounted to be stationary or movable, e.g. in translation, in order to complete the connection with the complementary coupling member 61. Naturally, the coupling members 60, 61 may be of any type and of any kind. By way of example, these coupling members 60, 61 may be optical fibers (optionally associated with optical elements), electrical cables, tubes for passing a fluid or passing a member, etc.

From the above description, it can be seen that the connection and disconnection system 4 is capable of providing one or more mechanical connections in translation and/or rotation and also one or more optical, electrical, or fluid-flow connections, and/or one or more mechanical passages. Naturally, the support 3 may include a multitude of hooks 36 and coupling members 60 so as to be adapted to receive successively one or advantageously a series of different medical instruments 2 using all or some of the mechanical or other connections.

In the above-described examples, the connection and disconnection system 4 has a single cam 29 for coupling together one or more actuator rods. Naturally, a support may be provided that is fitted with a plurality of engagement cams for one or more actuator rods.

The invention is not limited to the embodiments described and shown since various modifications may be applied thereto without going beyond the ambit of the invention.

What is claimed is:

1. A medical appliance comprising a medical instrument (2) separable from an actuator support (3), the appliance including a connection and disconnection system (4) between the instrument (2) and the support (3), and being characterized in that the connection and disconnection system comprises:

a connector (6) carried by the instrument and including a guide (9) for actuator rods (11) held resiliently by return springs (17) in the guide by heads (12) projecting from the free end of the guide, the connector (6) being provided with a rotary coupling member (20) and having a transverse end face ($9_1$) on which the heads (12) are held pressed against the transverse end face ($9_1$) by the return springs (17); and a connection endpiece (7) of longitudinal axis (Y) carried by the support and including a cam engagement (29) in the form of a disk guided in rotation in a plane perpendicular to the longitudinal axis (Y), reception setbacks (30) being arranged in the cam engagement (29) and distributed in an angular disposition that is identical to that of the head (12) of the actuator rods (11) that are to penetrate together into the insides of the setbacks (30), the cam engagement (29) being fitted with a rotary coupling member (33) complementary to the rotary coupling member (20) presented by the connector (6), the endpiece (7) also presenting hooks (36) connected to an actuator system (37), each hook (36) including a housing (38) for receiving the head (12) of the actuator rod (11), the hooks (36) being arranged in such a manner that the housings (38) are in alignment in a common plane extending transversely to the longitudinal axis (Y), the cam engagement (29) being engaged in at least some of the housings (38), while the setbacks (30) of the cam extend outside the hooks (36) to receive the heads (12) of the actuator rods (11), the endpiece (7) and the connector (6) occupying a connection position after they have approached each other axially, leading firstly to rotary coupling between the connector (6) and the engagement cam (29) and secondly to disengagement of the head (12) of the rod from the transverse end face ($9_1$) of the guide (9) so that said head (12) is engaged inside the reception setback (30) presented by the engagement cam, axial approach being followed by a movement in rotation between the connector (6) and the connection endpiece (7) to turn the engagement cam (29) relative to the actuator hooks (36) so as to move the head (12) of the rod until it co-operates with the hook (36) in order to provide a mechanical connection between the head (12) of the rod and the actuator hook (36).

2. A medical appliance according to claim 1, characterized in that at least one hook (36) possesses a reception housing (38) for receiving a head (12) of the rod in order to provide a connection in translation between the rod (11) and the actuator hook (36).

3. A medical appliance according to claim 1, characterized in that at least one hook (36) possesses a housing of prismatic shape suitable for receiving a complementary prismatic head (12) of a rod in order to provide a connection in translation and/or rotation between the rod (11) and the actuator hook (36).

4. A medical appliance according to claim 2, characterized in that the hook (36) possesses a positioning groove (41) for the rod, which groove is formed between the reception housing (38) for the head and the free end of the hook.

5. A medical appliance according to claim 1, characterized in that the connection endpiece (7) is provided with at least one optical, electrical, fluid-flow, or mechanical-passage coupling member (60), and in that the guide (9) of the connector is provided with at least one complementary coupling member (61) that is respectively optical, electrical, fluid-flow, or for providing mechanical passage, that is adapted to be aligned with the coupling member (60) of the endpiece as a result of establishing mechanical connection between the rod (11) and the actuator hook (36).

6. A medical appliance according to claim 5, characterized in that the coupling member (60) passes through the engagement mechanism (29) via a setback (30) adapted to ensure that said member (60) is not moved by the engagement mechanism when it turns, said member (60) being located substantially at the free end of the hook.

7. A medical appliance according to claim 1, characterized in that the support (3) includes a body (52) that is cutout to present a series of bars (53), at least one of which is movable linearly relative to the other bars, thereby constituting a slideway-forming part of the system (37) for actuating a hook (36).

8. A medical appliance according to claim 7, characterized in that each slideway-forming bar (53) is provided with a hook (36) at one of its ends, while its other end is connected to a translation actuator member.

9. A medical appliance according to claim 7, characterized in that at least one bar (53) incorporates an actuator system for actuation in rotation and/or in translation.

10. A medical appliance according to claim 7, characterized in that at least one bar (53) serves to position an optical, electrical, fluid-flow, or mechanical-passage coupling member.

11. A medical appliance according to claim 1, characterized in that the connector (6) and the connection endpiece (7) include angular indexing means enabling them to be aligned in a predetermined position for their axial approach.

12. A medical appliance according to claim 11, characterized in that the connector (6) and the endpiece (7) include guide means (42, 43, 44) for providing guidance in sliding for the axial approach and then in rotation to an abutment position corresponding to the connected position of the connection and disconnection system (4).

13. A medical appliance according to claim 1, characterized in that the connector (6) and the endpiece (7) include locking means for locking the connector and the endpiece in their connected position.

14. A medical appliance according to claim 12, characterized in that the locking means (42, 43, 44) include a single-use locking indicator carried by the connector, which means serve, after the instrument has been disconnected following use, to prevent reconnection of the instrument to the support.

15. A medical appliance according to claim 13, characterized in that the locking means include a reusable locking indicator that is carried by the connector (6) or by the coupling endpiece (7), and that acts, after disconnection of the instrument (2), to enable the instrument to be reconnected to the support (3).

16. A medical appliance according to claim 1, characterized in that the actuator rod (11) is a flexible element such as a cable, or a rigid element such as a rigid shaft.

17. A medical appliance according to claim 1, characterized in that the separable medical instrument constitutes all or part of a surgical tool, a catheter, an endoscope, or a probe.

18. A medical appliance according to claim 16, characterized in that the medical instrument (2) is an endoscope or a catheter including a tubular sheath (G) fastened to the connector (6) and having at least one actuator rod (11) fastened to the end thereof for steering the head of the sheath.

19. A medical appliance according to claim 18, characterized in that the tubular sheath (G) includes at least one optical, electrical, fluid-flow, or mechanical-passage coupling member (61) for single use and complementary to at least one respective optical, electrical, fluid-flow, or mechanical-passage coupling member (60) mounted in the coupling endpiece (7).

* * * * *